United States Patent
Kurdyumov et al.

(10) Patent No.: US 9,629,945 B2
(45) Date of Patent: Apr. 25, 2017

(54) STILBENE-BASED REACTIVE COMPOUNDS, POLYMERIC MATRICES FORMED THEREFROM, AND ARTICLES VISUALIZABLE BY FLUORESCENCE

(71) Applicant: SurModics, Inc., Eden Prairie, MN (US)

(72) Inventors: Aleksey V. Kurdyumov, Lino Lakes, MN (US); Dale G. Swan, Saint Louis Park, MN (US); Nathan A. Lockwood, Minneapolis, MN (US); Bruce M. Jelle, Chanhassen, MN (US)

(73) Assignee: SURMODICS, INC., Eden Prairie, MN (US)

( * ) Notice: Subject to any disclaimer, the term of this patent is extended or adjusted under 35 U.S.C. 154(b) by 523 days.

(21) Appl. No.: 14/104,208

(22) Filed: Dec. 12, 2013

(65) Prior Publication Data

US 2014/0162083 A1 Jun. 12, 2014

Related U.S. Application Data

(60) Provisional application No. 61/736,436, filed on Dec. 12, 2012.

(51) Int. Cl.
| | |
|---|---|
| C07C 233/81 | (2006.01) |
| C07C 271/58 | (2006.01) |
| C07C 309/51 | (2006.01) |
| A61L 31/14 | (2006.01) |
| A61L 31/10 | (2006.01) |
| C07D 251/68 | (2006.01) |
| C07C 235/84 | (2006.01) |
| C07C 309/46 | (2006.01) |
| A61B 1/005 | (2006.01) |
| C07D 251/54 | (2006.01) |
| A61B 1/00 | (2006.01) |

(52) U.S. Cl.
CPC .............. *A61L 31/14* (2013.01); *A61B 1/005* (2013.01); *A61L 31/10* (2013.01); *C07C 235/84* (2013.01); *C07C 309/46* (2013.01); *C07D 251/54* (2013.01); *C07D 251/68* (2013.01); *A61B 1/00135* (2013.01); *Y10T 428/31942* (2015.04)

(58) Field of Classification Search
CPC ... C07C 233/81; C07C 271/58; C07C 309/61; A61L 31/14
USPC ............. 562/51, 27; 564/154; 568/306, 325; 428/524; 523/105
See application file for complete search history.

(56) References Cited

U.S. PATENT DOCUMENTS

| | | |
|---|---|---|
| 5,002,582 A | 3/1991 | Guire et al. |
| 5,414,075 A | 5/1995 | Swan et al. |
| 5,563,056 A | 10/1996 | Swan et al. |
| 5,637,460 A | 6/1997 | Swan et al. |
| 5,714,360 A | 2/1998 | Swan et al. |
| 5,807,605 A | 9/1998 | Tingey et al. |
| 5,821,287 A | 10/1998 | Hu et al. |
| 5,858,653 A | 1/1999 | Duran et al. |
| 6,156,345 A | 12/2000 | Chudzik et al. |
| 6,211,374 B1 | 4/2001 | Ippoliti |
| 6,278,018 B1 | 8/2001 | Swan |
| 6,362,248 B1 | 3/2002 | Hara et al. |
| 6,410,044 B1 | 6/2002 | Chudzik et al. |
| 7,052,512 B2 | 5/2006 | Yang et al. |
| 7,056,533 B2 | 6/2006 | Chudzik et al. |
| 7,429,623 B2 | 9/2008 | Molock et al. |
| 7,592,418 B2 | 9/2009 | Pathak et al. |
| 7,772,393 B2 | 8/2010 | Guire et al. |
| 7,820,072 B2 | 10/2010 | Hsieh et al. |
| 8,349,452 B2 | 1/2013 | Jung et al. |
| 2005/0254003 A1 | 11/2005 | Jani et al. |
| 2006/0287410 A1 | 12/2006 | Chudzik et al. |
| 2007/0197750 A1 | 8/2007 | Gibanel et al. |
| 2008/0261323 A1 | 10/2008 | Diamond et al. |
| 2010/0198168 A1 | 8/2010 | Rooijmans et al. |
| 2011/0046255 A1 | 2/2011 | Rooijmans et al. |
| 2011/0059874 A1 | 3/2011 | Rooijmans et al. |
| 2011/0144373 A1 | 6/2011 | Swan et al. |
| 2011/0245367 A1 | 10/2011 | Kurdyumov et al. |
| 2012/0082713 A1 | 4/2012 | Meyering et al. |
| 2012/0149934 A1 | 6/2012 | Kurdyumov et al. |
| 2013/0143056 A1 | 6/2013 | Swan et al. |

FOREIGN PATENT DOCUMENTS

| | | |
|---|---|---|
| EP | 1156075 | 11/2001 |
| WO | WO 97/22037 | 6/1997 |
| WO | WO 01/02449 | 1/2001 |
| WO | WO 01/90268 | 11/2001 |
| WO | WO 03/022322 | 3/2003 |
| WO | WO 03/030879 | 4/2003 |
| WO | WO 03/061631 | 7/2003 |

(Continued)

OTHER PUBLICATIONS

Siegrist, A.E., et al., (2012) *Optical Brighteners*, Ullmann's Encyclopedia of Industrial Chemistry 25: 427-449.

*Primary Examiner* — Venkataraman Balasubramanian (74) *Attorney, Agent, or Firm* — Kagan Binder, PLLC (57) ABSTRACT

The invention is directed to latent reactive and polymerizable derivatives of fluorescent stilbene-based compounds. The compounds can be used to provide articles with a fluorescence property, such as medical devices (e.g., catheters). The fluorescent compounds can be used in association with polymers, or can be incorporated into polymers, and the polymers used in a coating composition on the article surface. The compounds allow for visual or machine inspection of coating properties such as uniformity of coverage.

6 Claims, 1 Drawing Sheet

(56) References Cited

FOREIGN PATENT DOCUMENTS

| WO | WO 2004/056406 | 7/2004 |
| WO | WO 2006/119328 | 11/2006 |
| WO | WO 2007/027479 | 3/2007 |
| WO | WO 2009/112548 | 9/2009 |
| WO | WO 2010/039653 | 4/2010 |
| WO | WO 2012/006135 | 1/2012 |

Fig. 1A
(normal light)

Fig. 1B
(long wave UV)

STILBENE-BASED REACTIVE COMPOUNDS, POLYMERIC MATRICES FORMED THEREFROM, AND ARTICLES VISUALIZABLE BY FLUORESCENCE

The present non-provisional application claims the benefit of commonly owned provisional Application having Ser. No. 61/736,436, filed on Dec. 12, 2012, entitled STILBENE-BASED REACTIVE COMPOUNDS, POLYMERIC MATRICES FORMED THEREFROM, AND ARTICLES VISUALIZABLE BY FLUORESCENCE, which application is incorporated herein by reference in its entirety.

FIELD

The invention relates to hydrophilic polymeric coatings for surfaces of medical articles and hydrophilic polymer coatings that can be visualized with light.

BACKGROUND

Developments in medicine have enabled the use of many non-classical surgical techniques in the treatment of diseases and disorders. For example, significant advances in implantable medical devices have enabled a host of new treatment options for patients. Early implantable medical devices were limited to surgical grade metals and were primarily used for gross mechanical repairs such as bone securement or replacement. However, in the last three decades, implantation of temporary or permanent structural and functioning elements has become commonplace, and such devices have become more intricate and complex in their structure and function.

The surfaces of implantable medical devices are of particular interest for a variety of reasons. Medical device surfaces represent the interface between the device material and the body fluid or tissue, and surface properties of the device can have a significant effect on how the device functions in the body. In many cases the device can provide a surface having one or more properties selected from lubricity and wettability, passivity against protein absorption, antimicrobial properties, drug delivery, biocompatibility, and hemocompatibility. Biocompatible polymers have been used to prepare polymeric matrices formed on the surface of the device (e.g., in the form of a coating) that have one or more of these properties.

The demand for medical articles having these types of coatings has appreciated because they generally improve the function of the device upon implantation or insertion in the body. For example, a lubricious polymeric coating can reduce frictional forces when the device is introduced and moved within the body. Various catheter types are examples of medical articles that may be provided with hydrophilic coatings.

Detection of a part, or all, of the medical device surface can be useful in manufacturing. For example, detection can allow one to understand the thickness of the coating and the uniformity and completeness of coating coverage on the device.

However, one problem is that many coatings applied to an implantable medical device are transparent and otherwise difficult to detect. And although reagents such as colorants and dyes are available, there are challenges regarding using such reagents to provide modified surfaces, such as in the form of coatings, that have one or more properties such as durability, biocompatibility, while preventing the compound from being lost from the surface, such as by leaching.

Further, detection reagents may not be biocompatible, may not be compatible with the material surface or polymeric material used to form a coating on the surface, may not immobilize properly on the surface or have a propensity to be lost or leached from a coating, or may not have properties useful for detection after immobilized on the surface. Detectable reagents such as radioisotopes or paramagnetic material may not be desirable for use in the body or may require elaborate equipment for their detection.

The inventors have prepared new and inventive compounds capable of being immobilized on a surface and visualized by fluorescence. The compounds are useful for preparing modified surfaces of medical devices, but can also be used for preparing visualizable surfaces outside of the medical device area.

SUMMARY

The current invention relates to fluorescent compounds having a stilbene-based fluorescent group, and a latent reactive or polymerizable group that permits covalent bonding of the fluorescent compound. The fluorescent compounds of the invention can be used to provide a fluorescent property to an article or material, such as a medical device.

In exemplary uses, fluorescent compounds of the invention can be applied to, or incorporated into, an article or material and then treated to cause covalent bonding of the fluorescent compound. The article or material treated can be one used for treatment of the body, such as an implantable medical device or article, or one that is used outside of the body. Articles and uses outside the body include biosensors, cell culture articles, bioassay materials, chemical analysis materials, and tissue and cell detection equipment.

In some aspects, the invention provides a compound of Formula I:

In formula I, $R^{A1}$, $R^{A1'}$, $R^{A2}$, $R^{A2'}$ and are independently selected from the group consisting of H and $-SO_3R^1$; and wherein $R^1$ is independently selected from the group consisting of H, monovalent, and divalent metal cations.

In a first embodiment of Formula I (subformula Ia), $R^B$ is:

and $R^{B'}$ is wherein $R^2$, $R^{2'}$, $R^3$ and $R^{3'}$ are with $R^6$ and $R^7$ being independently selected from H, $R^8R^{23}R^9$, $R^8R^{10}$, phenyl, and substituted phenyl:

wherein $R^{11}$ and $R^{11'}$ are selected from the group consisting of H, hydrocarbyl groups, and —SO$_3$R$^1$, with the proviso that both $R^6$ and $R^7$ are not H; wherein $R^8$ is a -(a covalent bond) or a C1-C8 hydrocarbylene group optionally containing one or more heteroatoms; wherein $R^{23}$ is selected from the group consisting of a covalent bond, —C(O)—, —CH$_2$NHC(O)—, —CH$_2$OC(O)O—, —CH$_2$NHC(S)NH—, —CH$_2$OC(S)NH—, —CH$_2$NHC(O)O—, —CH$_2$NHC(O)NH—, —CH$_2$OC(O)—, and —C(O)O—; with the proviso that R8 and R23 are not both covalent bonds; wherein $R^9$ is selected from a photochemically reactive diaryl ketone group optionally ring substituted, a thermochemically reactive group selected from the group consisting of aryl azides, acyl azides, azido formats, phosphoryl azides, diazoalkanes, diazoketones, diazirines, ketenes, dialkyl peroxides, diacyl peroxides, and peroxyesters, or a free radical polymerizable group selected from acrylate, methacrylate, hydroxyethyl methacrylate, hydroxyethyl acrylate, hydroxypropyl acrylate, hydroxypropyl methacrylate, glyceryl acrylate, glyceryl methacrylate, acrylamino, methacrylamino, alkyl(meth)acrylamino, aminoalkyl(meth)acrylamino, vinyl ether, and vinyl ester; and wherein $R^{10}$ is selected from the group consisting of —H, —OH, —NH$_2$, —C(O)NH$_2$, —C(O)OR$^1$ wherein $R^1$ is defined herein; and where, in $R^2$, $R^{2'}$, $R^3$, and $R^{3'}$, at least one of $R^6$ and/or $R^7$ includes $R^9$; with the proviso that $R^6$ and $R^7$ are not both —H.

In a second embodiment of Formula I (subformula Ib), $R^{A1}$, $R^{A1'}$, $R^{A2}$, $R^{A2'}$ are as described in the first embodiment above, and $R^B$ and $R^{B'}$ are wherein $R^{14}$ and $R^{15}$ are independently selected from H and $R^{23}R^9$ wherein $R^{23}$ and $R^9$ are as described above and at least one of $R^{14}$ or $R^{15}$ is $R^{23}R^9$, with the proviso that both $R^{14}$ and $R^{15}$ are not H.

In a third embodiment of Formula I (subformula Ic), $R^{A1}$, $R^{A1'}$, $R^{A2}$, $R^{A2'}$ are as described in the first embodiment and wherein $R^B$ and $R^{B'}$ are selected from the group consisting of:

$R^8R^{23}R^9$, and $R^{23}R^9$, wherein $R^8$, $R^{23}$ and $R^9$ are as described above.

Other embodiments of the invention are directed to methods for preparing compounds of Formula I. One method provides a compound of the first embodiment of Formula I (subformula Ia). The method comprises a step of reacting a compound of formula V:

wherein $R^{22}$, $R^{22'}$, $R^{22'''}$, and $R^{22''''}$ are independently selected from H and $R^8R^{10}$, with the proviso that $R^{22}$ and $R^{22'}$ are not both H and that $R^{22'''}$ and $R^{22''''}$ are not both H; and wherein $R^1$, $R^4$, $R^5$, $R^8$, and $R^{10}$ are as described in subformula Ia, with an isocyanate derivatized diaryl ketone.

Another method to provides a compound of the first embodiment of Formula I (subformula Ia) comprises one or more steps of reacting reactant compounds, where the reactant compounds comprise (a) a 2,4,6-trihalo-1,3,5-triazine; (b) a diaminostilbenedisulfonic acid or salt thereof, (c) a primary amine derivatized diaryl ketone, optionally ring substituted; and (d) a compound of the formula $R^{10}R^8NHR^{10'}R^{23'}$, wherein $R^8$ is a C1-C8 hydrocarbylene group optionally containing one or more heteroatoms, and $R^{10}$ and $R^{23}$ are as described above.

Other aspects of the invention provide a polymer prepared using a compound of Formula I. For example, where group $R^9$ of the compound of Formula I is selected from a free radical polymerizable group (e.g., acrylate, methacrylate, etc.) the compound can be a free radically polymerizable monomer, which can be copolymerized with one or other monomers to provide a copolymer. The compound can include one or more free radical polymerizable group(s).

In some aspects the invention provides a polymeric matrix comprising the compound of Formula I, or a polymeric matrix including a polymer prepared using the compound of Formula I. For example, the polymeric matrix can include a compound of Formula I with one or more photo reactive or thermally reactive groups that have been covalently bonded to a polymeric material in the matrix. In some cases, the compound has two or more (photo or thermally) reacted groups that crosslink polymeric material together in the matrix. In some aspects the polymeric matrix includes a polymer prepared from a compound of Formula I wherein $R^9$ is a free radical polymerizable group. Exemplary polymeric matrices are formed using a composition that includes a hydrophilic polymer and a compound of Formula I, or a hydrophilic polymer made using a compound of Formula I, or both.

In some modes of preparation, the polymeric matrix is prepared by treating a composition comprising a compound of Formula I with UV light, or heat, to activate the latent reactive group to cause covalent bonding to the polymeric material, or another material that the composition is in association with. For example, the method of forming a polymeric matrix can include steps of obtaining a composition comprising a compound of Formula I having a diaryl ketone group, or the polymer made using a compound of Formula IV having a diaryl ketone group, and then treating the composition with ultraviolet light in the range of 320 nm to 350 nm to activate the diaryl ketone group to provide covalent bonding to a target molecule.

In other modes of practice, a polymeric matrix is formed by immobilizing a compound of Formula I on a surface by applying and treating the compound on the surface, contacting the immobilized compound with a composition comprising polymerizable material, and then treating the surface again to activate the compound of Formula I to cause polymerization of the polymerizable material and formation of the polymeric matrix.

In exemplary embodiments the diaryl ketone group undergoes covalent bonding to a target in the matrix, or to a material that the matrix is in contact with. The resulting covalent bonding can cause one or more of the following: immobilization of the compound of the polymeric matrix, crosslinking of polymeric material in the polymeric matrix, bonding of covalent material to a material the matrix is in contact with, and/or bonding of the compound to a material the matrix is in contact with.

In some aspects the polymeric matrix is in the form of all or a portion of the body member of an implantable medical device, or in the form of a coating on an implantable medical device. For example, in some aspects the invention provides an implantable medical device comprising a hydrophilic coating, the hydrophilic coating comprising a compound of Formula I.

Compounds and polymeric matrices of the invention can also be described in terms of properties associated with the matrix. For example, in other embodiments the invention also provides a medical device comprising a hydrophilic coating, the hydrophilic coating comprising a compound comprising first and second photo functionalities, the first photo functionality being a chemical structure that absorbs ultraviolet light in the range of 300 nm to 430 nm and remits absorbed energy as blue fluorescent light in the range of 400 nm to 500 nm; and the second photo functionality being a chemical structure that absorbs ultraviolet light in the range of 320 nm to 350 nm, the chemical structure resulting in the initial formation of an excited singlet state that undergoes intersystem crossing to an excited triplet state, with the excited triplet capable of inserting into a carbon-hydrogen bond by abstraction of a hydrogen atom, thus creating a radical pair.

Another embodiment of the invention provides a medical device comprising a hydrophilic coating, the hydrophilic coating comprising an aryl ketone derivative of a triazinylaminostilbenesulfonic acid.

Other embodiments of the invention include methods for visualizing a matrix or a surface comprising a compound of Formula I. If the matrix is intended for use in the body, the method can include steps of inspecting the matrix prior to insertion of the device in the body. For example, the method can include a step or irradiating the matrix coating using a wavelength that results in excitation of the stilbene moiety of the compound, and emission of colored light from the matrix.

The invention also provides, in some embodiments, a method for visualizing a polymeric matrix or visualizing a medical device coating. The method comprises steps of obtaining the polymeric matrix or medical device coating comprising a compound of Formula I or a polymer prepared using the compound of Formula I, and a step of irradiating the matrix or coating with light in the range of 300 nm to 430 nm and observing the fluorescent light remitted from the matrix or coating.

Compounds of the invention are useful for a number of purposes, including assessing the quality or location of a device coating during manufacture, or during a medical procedure. For example, the coating can be monitored during manufacturing or prior to use to provide information relating to coating properties such as uniformity and thickness. In some embodiments, a coating can be visualized prior to insertion and manipulation of the medical device within the patient so the coating's location on the device is understood. The coating including a compound of Formula I can also include a hydrophilic polymer to provide a lubricious surface which facilitates movement of the device in the body.

In exemplary embodiments the polymeric matrix comprises a compound of Formula I and a hydrophilic polymer comprising vinyl pyrrolidone. In exemplary embodiments the matrix is in the form of a coating on the surface of a medical device. The medical device can be exemplified by, but not limited to, cardiac or urethral catheters, or an endoscope, such as urogenital endoscope.

Other embodiments of the invention include methods for treating a patient using a device comprising a coating formed from a polymeric matrix including a compound of Formula I. Exemplary treatments include those involving the vasculature or cardiac tissue, such as angioplasty, angiography, and balloon septostomy.

DETAILED DESCRIPTION

The embodiments of the present invention described herein are not intended to be exhaustive or to limit the invention to the precise forms disclosed in the following detailed description. Rather, the embodiments are chosen and described so that others skilled in the art can appreciate and understand the principles and practices of the present invention.

All publications and patents mentioned herein are hereby incorporated by reference. Where any inconsistencies exist between these documents incorporated by reference and this disclosure, for example in the definition of terms, this disclosure is to govern. The publications and patents disclosed herein are provided solely for their disclosure. Nothing herein is to be construed as an admission that the inventors are not entitled to antedate any publication and/or patent, including any publication and/or patent cited herein.

Compounds of Formula I of the invention include a stilbene chemical moiety and a latent reactive or polymerizable chemical moiety. Stilbene chemical moieties are a part of fluorescent compounds known in the art as "optical brighteners" or "fluorescent brighteners" such as those listed in "Optical Brighteners," Siegrist et al. (Ullmann's Encyclopedia of Industrial Chemistry, Wiley, 2012). Optical brighteners are typically dyes that absorb light in the 340-370 nm range (ultraviolet and violet region) and re-emit light in the 420-470 nm region (blue region).

In some cases, the latent reactive moiety of the Compounds of Formula I is a UV activatable group. Latent UV activatable groups respond to specific applied UV radiation to undergo active species generation with resultant covalent bonding to a target, such as the material of an article surface, or a polymer that is present in mixture with the compound.

A "latent reactive group", as used herein, refers to a chemical group that responds to an applied external energy source in order to undergo active specie generation, resulting in covalent bonding to an adjacent chemical structure. Preferred groups are sufficiently stable to be stored under conditions in which they retain such properties. See, e.g., U.S. Pat. No. 5,002,582, the disclosure of which is incorporated herein by reference. Latent reactive groups can be chosen that are responsive to various portions of the electromagnetic spectrum, with those responsive to ultraviolet and visible portions of the spectrum (referred to herein as "photoreactive") being particularly preferred.

Photoreactive aryl ketones such as acetophenone and benzophenone, or their derivatives, are preferred, since these functional groups, typically, are readily capable of undergoing the activation/inactivation/reactivation cycle described herein. Benzophenone is a particularly preferred photoreactive group, since it is capable of photochemical excitation with the initial formation of an excited singlet state that undergoes intersystem crossing to the triplet state. The excited triplet state can insert into carbon-hydrogen bonds by abstraction of a hydrogen atom (from a support surface, for example), thus creating a radical pair. Subsequent collapse of the radical pair leads to formation of a new carbon-carbon bond. If a reactive bond (e.g., carbon-hydrogen) is not available for bonding, the ultraviolet light-induced excitation of the benzophenone group is reversible and the molecule returns to ground state energy level upon removal of the energy source. Hence, photoreactive aryl ketones are particularly preferred.

Another type of latent reactive group is a "thermally-reactive groups" which refer to classes of compounds that decompose thermally to form reactive species that can form covalent bonds. The covalent bonds can allow the stilbene-based derivative to bond to a target chemical structure. Both carbenes and nitrenes possess reactive electron pairs that can undergo a variety of reactions, for example, including carbon bond insertion, migration, hydrogen abstraction, and dimerization. Examples of carbene generators include diazirines and diazo-compounds. Examples of nitrene generators include aryl azides, particularly perfluorinated aryl azides, acyl azides, and triazolium ylides. In addition, groups that upon heating form reactive triplet states, such as dioxetanes, or radical anions and radical cations, can be used to as the thermally-reactive group. Generally these compounds thermally decompose at temperatures of not more than 200° C.

In some embodiments the fluorescent compound includes a free radical polymerizable group. In a free radical reaction, reaction the polymerizable group can react with other polymerizable groups. A preferred polymerizable group is an ethylenically unsaturated group. Exemplary polymerizable groups include methacrylate, hydroxyethyl methacrylate, hydroxyethyl acrylate, hydroxypropyl acrylate, hydroxypropyl methacrylate, glyceryl acrylate, glyceryl methacrylate, acrylamino, methacrylamino, alkyl(meth)acrylamino, and aminoalkyl(meth)acrylamino, vinyl ether, and vinyl ester.

As a general matter compounds of the invention are based on the following stilbene-containing Formula I:

In formula I, $R^{A1}$, $R^{A1'}$, $R^{A2}$, $R^{A2'}$ and are independently selected from the group consisting of H and —$SO_3R^1$; and wherein $R^1$ is independently selected from the group consisting of H, monovalent, and divalent metal cations. In some more specific aspects $R^{A1'}$ and $R^{A2'}$ are H, and $R^{A1}$ and $R^{A2}$ are —$SO_3R^1$ with $R^1$ being a monovalent metal cation such as sodium.

In some more specific aspects, the —$SO_3R^1$ groups are positioned on the ring as follows:

In subformula Ia of Formula I, $R^B$ is and $R^{B'}$ is:

with $R^2$, $R^{2'}$, $R^3$ and $R^{3'}$ being and with $R^6$ and $R^7$ being independently selected from H, $R^8R^{23}R^9$, $R^8R^{10}$, phenyl, or substituted phenyl:

with $R^{11}$ and $R^{11'}$ being selected from the group consisting of H, hydrocarbyl groups, and —$SO_3R^1$, with the proviso that both $R^6$ and $R^7$ are not H. $R^8$ is a -(a covalent bond) or a C1-C8 hydrocarbylene group optionally containing one or more heteroatoms. $R^{23}$ is selected from the group consisting of a covalent bond, —C(O)—, —CH$_2$NHC(O)—, —CH$_2$OC(O)O—, —CH$_2$NHC(S)NH—, —CH$_2$OC(S)NH—, —CH$_2$NHC(O)O—, —CH$_2$NHC(O)NH—, —CH$_2$OC(O)—, and —C(O)O—. R8 and R23 are not both covalent bonds.

In some cases $R^9$ is selected from a photochemically reactive diaryl ketone group optionally ring substituted. In some cases $R^9$ is selected from a thermochemically reactive group selected from the group consisting of aryl azides, acyl azides, azido formats, phosphoryl azides, diazoalkanes, diazoketones, diazirines, ketenes, dialkyl peroxides, diacyl peroxides, and peroxyesters. In some cases $R^9$ is selected from a free radical polymerizable group selected from acrylate, methacrylate, hydroxyethyl methacrylate, hydroxyethyl acrylate, hydroxypropyl acrylate, hydroxypropyl methacrylate, glyceryl acrylate, glyceryl methacrylate, acrylamino, methacrylamino, alkyl(meth)acrylamino, aminoalkyl(meth)acrylamino, vinyl ether, and vinyl ester; and wherein $R^{10}$ is selected from the group consisting of —H, —OH, —NH$_2$, —C(O)NH$_2$, and —C(O)OR$^1$ wherein $R^1$ is defined herein; and where, in $R^2$, $R^{2'}$, $R^3$, and $R^{3'}$, at least one of $R^6$ and/or $R^7$ includes $R^9$; with the proviso that $R^6$ and $R^7$ are not both —H.

Within subformula Ia are included subformula Ia-1 and Ia-2 and subformula Ia-2

In subformulas Ia-1 and Ia-2 $R^6$ and $R^7$ are independently selected from H and $R^8R^{10}$, wherein $R^8$ and $R^{10}$ are as defined in Formula I.

In more specific aspects of compounds of Formula I, Ia, Ia-1, and Ia-2, $R^8$ is a C1-C4 hydrocarbylene group, $R^8$ is a C2 hydrocarbylene group, $R^{10}$ is —OH, and/or $R^6$ and $R^7$ are phenyl.

Exemplary compounds of Formula I, Ia, Ia-1, or Ia-2 include compound 4 and compound 5:

In some embodiments, methods for methods for the preparation of subformula Ia include step of reacting a compound of formula V:

wherein $R^{22}$, $R^{22'}$, $R^{22'''}$, and $R^{22''''}$ are independently selected from H and $R^8R^{10}$, with the proviso that $R^{22}$ and $R^{22'}$ are not both H and that $R^{22'''}$ and $R^{22''''}$ are not both H; and wherein $R^1$, $R^4$, $R^5$, $R^8$, and $R^{10}$ are as described in subformula Ia, with an isocyanate derivatized diaryl ketone.

In some modes of practice, the isocyanate derivatized diaryl ketone has the following structure:

Therefore, embodiments of the invention provide aryl ketone derivatives of a triazinylaminostilbenesulfonic acid, for example, aryl ketone derivatives of 1,3,5-triazinyl-containing stilbene compounds such as aryl ketone derivatives of 2,2'-(1,2-ethenediyl)bis[5-[[4-[bis(2-hydroxyethyl)amino]-6-(phenylamino)-1,3,5-triazin-2-yl]amino]-benzenesulfonic acid, disodium salt (see, for example compound 5 of Example 4). The aryl ketone derivatives of a triazinylaminostilbenesulfonic acid can be included in a hydrophilic coating on a medical device, as described herein.

Another method to provides a compound of subformula Ia comprises one or more steps of reacting reactant compounds, where the reactant compounds comprise (a) a 2,4,6-trihalo-1,3,5-triazine; (b) a diaminostilbenedisulfonic acid or salt thereof, (c) a primary amine derivatized diaryl ketone, optionally ring substituted; and (d) a compound of the formula $R^{10}R^8NHR^{10'}R^{23'}$, wherein $R^8$ is a C1-C8 hydrocarbylene group optionally containing one or more heteroatoms, and $R^{10}$ and $R^{23}$ are as described above.

In more specific modes of practice, reactant compound (a) is 2,4,6-trichloro-1,3,5-triazine (cyanuric chloride); reactant compound (b) is 4,4'-diaminostilbene-,2,2'-disulfonic acid; reactant compound (c) is 4-aminobenzophenone; in reactant compound (d) $R^8$ is a C1-C4 hydrocarbylene group; in reactant compound (d) $R^{10}$ is —OH; and/or reactant compound (d) is diethanolamine.

In a second embodiment of Formula I (subformula Ib), $R^{A1}$, $R^{A1'}$, $R^{A2}$, $R^{A2'}$ are as described in the first embodiment above, and $R^B$ and $R^{B'}$ are wherein $R^{14}$ and $R^{15}$ are independently selected from H and $R^{23}R^9$ wherein $R^{23}$ and $R^9$ are as described above and at least one of $R^{14}$ or $R^{15}$ is $R^{23}R^9$, with the proviso that both $R^{14}$ and $R^{15}$ are not H.

In more specific aspects of compounds of subformula Ib $R^{16}$ is —C(O)—.

An exemplary compound of Formula Ib is compound 6:

In a third embodiment of Formula I (subformula Ic), $R^{A1}$, $R^{A1'}$, $R^{A2}$, $R^{A2'}$ are as described in the first embodiment and wherein $R^B$ and $R^{B'}$ are selected from the group consisting of:

$R^{16}R^9$, and $R^{16}R^{21}R^9$, (wherein $R^{16}$ and $R^9$ are as described herein and $R^{21}$ is a C1-8 hydrocarbylene group optionally substituted with one or more heteroatoms. In more specific aspects of subformula Ic, $R^{16}R^{21}$ is —C(O)$R^{21}$—; $R^{21}$ is —NR$^{24}$—, or —NR$^{24}$N—, wherein $R^{24}$ is a C1-C8 hydrocarbylene group; $R^{21}$ is NR$^{24}$N; $R^{24}$ is a C1-C4 hydrocarbylene group.

In subformula Ic includes compounds of the subformula Ic-1:

compound 7:

and compound 8:

wherein $R^{25}$ is H or CH$_3$.

Exemplary compounds of subformula Ic include compound 3:

In some aspects compounds of Formula I can be described in terms of solubility properties. Solubility refers to the level to which a solute (e.g., a compound of Formula I) dissolves in a solvent. For a compound of Formula I in a particular solvent, "practically insoluble", or "insoluble" refers to having a solubility of 1 part compound per more than 10,000 parts of solvent, "very slightly soluble" refers to having a solubility of from 1 part compound per 1000 to 10,000 parts of solvent; "slightly soluble" refers to having a solubility of 1 part compound per from 100 to 1000 parts of solvent; "sparingly soluble" refers to having a solubility of 1 part compound from 30 to 100 parts of solvent; "soluble" refers to having a solubility of at least 1 part compound per from 10 to 30 parts solvent, "freely soluble" refers to having a solubility of at least 1 part compound per from 1 to 10 parts solvent, or "very soluble" refers to having a solubility of greater than 1 part compound per from 1 part solvent. These descriptive terms for solubility are standard terms used in the art (see, for example, *Remington: The Science and Practice of Pharmacy*, 20$^{th}$ ed. (2000), Lippincott Williams & Wilkins, Baltimore Md.). In aspects of the invention where a compound of Formula I is present in a composition along with a hydrophilic polymer for the preparation of a hydrophilic polymeric matrix, the compound may be soluble, freely soluble, or very soluble. The solubility, or lack thereof, of a compound of Formula I can be described in any desired solvent, such as water or an alcohol (e.g., isopropanol).

In some embodiments, a compound of Formula I is covalently bonded to a material or article to provide the material or article with a fluorescent property. In other embodiments the compound of Formula I is present in a polymeric matrix and can be bonded to polymeric material in the matrix. Some embodiments of the present disclosure are directed to polymeric matrices that can be visualized by fluorescence, and methods for preparing such visualizable matrices. In some cases the matrix is in the form of a coating on a medical device. The matrix, for example, can include a compound of Formula I, and a hydrophilic polymeric material.

The compound of Formula I can be bonded to material of a wide variety of medical devices or articles, or present in a polymeric matrix associated with a wide variety of medical devices or articles. Materials commonly used to fabricate the medical article or device include plastics (e.g., thermoplastics), metals, and ceramics. In order to describe aspects of the invention, materials that form the structure of the article (e.g., the tubing of catheter) are referred to herein as "device materials" (or "article materials") or whereas the materials used to form the polymeric coatings formed on the device, per se, are herein referred to as "coating materials." Device materials are commonly referred to as biomaterial(s) as the coated article is typically placed in contact with biological fluids or tissues, for example, but not limited to, following implantation in the body. Compounds of Formula I can be associated with the surface of any device material or any medical device as known in the art, alone, or along with other components such as polymers, including those exemplified herein.

Exemplary device materials on which a compound of Formula I can be associated with, alone or in a polymeric matrix, include plastic polymeric materials. Plastic polymeric materials include, but are not limited to, polyvinylchloride (PVC), polyethersulfone (PES), polysulfone (PS), polypropylene polyethylene, (PE), polyurethane (PU), polyetherimide (PEI), polycarbonate (PC), and polyetheretherketone (PEEK), poly amides (nylon), PEBAX®. Combinations of plastic polymeric materials can be used to form the device. The device may also be fabricated from one plastic polymeric material in one portion, and a different plastic polymeric material in another portion of the device. Thermoplastic polymeric materials can be formed into medical device using processes such as molding and extrusion using heat to melt the thermoplastics.

Device materials on which a compound of Formula I can be associated with, alone or in a polymeric matrix, also include metals, and metal combinations. Metals used in medical articles include, but are not limited to, platinum, gold, or tungsten, as well as other metals such as rhenium, palladium, rhodium, ruthenium, titanium, nickel, and alloys of these metals, such as stainless steel, titanium/nickel, nitinol alloys, and platinum/iridium alloys. These metals, including other alloys or combinations, can serve as suitable substrates on which a visualizable, hydrophilic coating can be formed.

Although many devices are constructed from substantially all metal materials, such as alloys, some may be constructed from both non-metal and metal materials, where at least a portion of the surface of the device can be metal. In some embodiments the metal surface can be a thin surface layer. Such surfaces can be formed by any method including sputter coating metal onto all or portions of the surface of the device.

Other surfaces that can be associated with a compound of Formula I can, alone or in a polymeric matrix, include those that include human tissue such as bone, cartilage, skin and teeth; or other organic materials such as wood, cellulose, compressed carbon, and rubber. Other contemplated biomaterials include ceramics including, but not limited to, silicon nitride, silicon carbide, zirconia, and alumina, as well as glass, silica, and sapphire. Combinations of ceramics and metals can also be coated.

The medical article, medical device or device can be any that is introduced temporarily or permanently into a mammal for the prophylaxis or treatment of a medical condition. These articles or medical devices include any that are introduced subcutaneously, percutaneously or surgically to be moved or rest within an organ, tissue, or lumen of an organ.

In some aspects a compound of Formula I can be associated with the surface of a catheter, alone or in a polymeric coating on the catheter surface. Exemplary catheters that can be associated with a compound of Formula I include, but are not limited to, guide catheters, urethral catheters, renal catheters, intravenous catheters, artificial lung catheters, blood pressure and stent graft catheters, atherectomy catheters, clot extraction catheters, percutaneous transluminal coronary angioplasty (PTCA) catheters, drug infusion catheters, angiographic catheters, neurological catheters such as neurovascular balloon catheters, thoracic cavity suction drainage catheters, electrophysiology catheters, stroke therapy catheters, abscess drainage catheters, central venous access catheters, hemodialysis catheters, and parental feeding catheters.

As another example, a compound of Formula I can be associated with the surface of an endoscopic sheath, alone or in a polymeric coating on the endoscopic sheath. Endoscopic sheaths can be used in various medical procedures, including those involving the urogenital tract, the gastrointestinal tract, and the vasculature. For example an endoscope can be delivered through an endoscopic sheath. A visualizable hydrophilic polymeric coating that is lubricious can facilitate movement of the sheath in the body as well as the device within the sheath.

In some aspects a compound of Formula I can be associated with the surface of a prosthetic device, alone or in a polymeric coating on the prosthetic device. Exemplary prosthetic devices include stents and grafts, such as small diameter grafts, vascular grafts, vascular stents (e.g., self-expanding stents), abdominal aortic aneurysm grafts, urological stents, and esophageal stents.

Other devices that can be associated with a compound of Formula I, along or in a polymeric matrix, include, but are not limited to, introducers (e.g., for guide catheters), electrostimulation (e.g., defibrillator or pacer) leads, defibrillators, biosensors, coronary guidewires, peripheral guidewires, vascular and non-vascular stylets, shunts (e.g., hydrocephalus, and cerebro-spinal fluid shunts), implanted drug infusion tubes, urological implants, urinary dilators, aneurysm exclusion devices, birth control devices, endoscopic devices, blood oxygenator tubing, biliary drainage products, catheter cuffs, tympanostomy vent tubes, and drainage tubes.

In some embodiments, the compound of Formula I is present in a hydrophilic coating that provides lubricity to a device surface so that it reduces the frictional forces associated with the movement of the device over tissue. A lubricious coating can be particularly useful for medical articles such as the catheters and endoscopic sheaths as described herein, which are moved within a lumen in the body.

Optionally, the medical device can have a "basecoat" of material between the device material (surface) and the compound of Formula I, or a coating that includes the compound of Formula I. The basecoat can facilitate formation of a coated layer that includes a hydrophilic polymer and the compound of Formula I. For example, the basecoat can provide an improved material surface on which the hydrophilic polymer can spread. The basecoat can also provide material to which the UV-activatable groups can covalently bond, by providing a source of abstractable hydrogens in the basecoat material. Exemplary basecoats can be formed from Parylene (polymers based on p-xylylene) using vapor phase polymerization as known in the art, or using a silane compound such as described in U.S. Pat. No. 6,706,408.

A composition for forming a polymeric matrix, such as a coating composition, can include one or more compounds of formula I and one or more polymeric materials. An appropriate solvent or solvent system can be chosen so the compound of formula I and polymeric materials can be dissolved. In some modes of practice the solvent system is water. In other modes of practice the solvent system includes an alcohol and water. Exemplary alcohols include short chain alcohols such as methanol, ethanol, and isopropanol. One solvent system uses a mixture of isopropanol and water. In some cases, the ratio of alcohol (e.g., isopropanol) to water can be in the range of about 10:90 to about 85:15, or about 15:85 to about 75:25, or about 25:75 to about 50:50.

The polymeric matrix-forming materials and compound of formula I can be dissolved in the solvent system in an amount sufficient to form a desired matrix, such as a device coating. For example, in some compositions the total concentration of the matrix-forming materials is in the range of from about 1% (w/v) to about 50% (w/v), or more specifically in the range about 1% (w/v) to about 5% (w/v), about 5% (w/v) to about 40% (w/v), about 1.5% (w/v) to about 15% (w/v), or about 2% (w/v) to about 10% (w/v).

The compound of formula I can be included in the composition to provide a desired amount of covalent bonding following activation of the latent reactive groups, a desired color and intensity of color in the formed matrix, or both. Some stilbene-based compounds provide a very intense color even at low concentrations in a material, and, therefore some embodiments of the present disclosure contemplate the use of very low amounts of compound in the matrix-forming compositions and formed matrices. For example, the concentration of the stilbene based compound can be about or 0.01 mg/mL or greater in the composition, with exemplary ranges of about 0.05 mg/mL to about 5 mg/mL, about 0.1 g/mL to about 2.5 mg/mL, or about 0.25 mg/mL to about 1 mg/mL.

In some embodiments, a crosslinking agent with two or more UV-activatable photogroups can be included in the coating composition at a concentration sufficient to provide crosslinking through covalent bonding the hydrophilic polymers and formation of a coated layer. Exemplary amounts of the cross-linking compound present in the coating composition range can be from about 0.01% to about 5%, from about 0.1% to about 1.0%, from about 0.01 to about 0.08%% to about or even about 0.01% to about 0.1% weight/volume (w/v). An exemplary amount of cross-linking agent added to the present coating composition can be about 0.05% weight/volume (w/v).

In one mode of practice, a coating composition can be prepared that includes a hydrophilic polymer, or a combination of hydrophilic polymers, and a compound of Formula I. In modes of practice, the composition is disposed on a device surface and then treated with UV light to activate the photogroups of the compound of Formula I resulting in covalent bonding and crosslinking the hydrophilic polymers to each other to form a polymeric matrix. The polymeric matrix provides a thin coated layer on the device surface with compound of Formula I serving to crosslink the polymeric material as well as provide a fluorescence visualization feature in the form of the stilbene moiety present in the compound.

Exemplary hydrophilic polymers, including hydrophilic homopolymers and copolymers, which can be synthetic or natural, that can be included in a matrix-forming composition along with a compound of Formula I are listed in the following Table 1. In some modes of practice, the hydrophilic polymer, or combination of hydrophilic polymers, can be dissolved at a concentration in the coating composition suitable for formation of a coating. The hydrophilic polymer concentration may depend on the type or types of polymers used, the solvent system, and desired coating properties (e.g., thickness). In some modes of practice, total hydrophilic polymer concentration (one or more hydrophilic polymers) in the range of about 1% (w/v) to about 50% (w/v), or more specifically in the range about 1% (w/v) to about 5% (w/v), or about 5% (w/v) to about 40% (w/v).

TABLE 1

| Hydrophilic polymers |
| --- |
| Synthetic hydrophilic polymers |
| Poly(acrylamide) (PA), poly(methacrylamide) (PMA), poly(vinylpyrrolidone) (PVP), poly(acrylic acid) (PAA), poly(ethylene glycol) (PEG), poly(vinyl alcohol) (PVA), poly(hydroxyethylmethacrylate) (PHEMA), poly(ethylene oxide), poly(ethyloxazoline), vinylpyrrolidone-methacrylamide copolymers, vinylpyrrolidone-acrylamide copolymers, and methyl vinyl ether-maleic anhydride copolymers. |
| Natural hydrophilic polymers |
| Heparin, heparan, hyaluronic acid, chondroitin, keratan, and dermatan, alginic acid, chitosan, cellulose, chitin, collagen, dextrans, pectins, and starch. |

A hydrophilic polymer is one that can be wetted and retain water. A wetted coating can provide the surface of the coated device article with lubricity, which refers to a characterization of the frictional force associated with a coating. A coating with improved lubricity has a lower frictional force. One or more components in the coating can also provide the coated material with durability. Durability refers to the wear resistance of a polymer coating, or the ability of a coating to adhere to a device surface when subjected to forces typically encountered during use (for example, normal force, shear force, and the like). Durability of a coating can be assessed by subjecting the device to conditions that simulate use conditions. The coating can be assessed by mechanical or physical challenge, such as manipulation of the coated device by bending, twisting, or turning, and/or when the device is in contact with a portion of the body or a portion of another medical article.

In some embodiments, the composition can optionally include a second compound having UV-activatable photogroups that is different than the compound of Formula I (i.e., with the first compound having UV-activatable photogroups represented by the compound of Formula I). For example, the second compound can lack a stilbene chemical moiety.

Exemplary optional second compound having UV-activatable photogroups include UV-activatable cross-linking agents having an ionic group that demonstrate solubility in an aqueous composition. In some embodiments, the UV-activatable cross-linking agent is a compound of formula VII:

$$X^1—Y—X^2 \quad (I)$$

where Y is a radical containing at least one acidic group, basic group, or a salt of an acidic group or basic group. $X^1$ and $X^2$ are each independently a radical containing a latent photoreactive group. Spacers can also be part of $X^1$ or $X^2$ along with the latent photoreactive group, such as an aryl ketone or quinine group. Exemplary acidic groups include, for example, sulfonic acids, carboxylic acids, phosphonic acids, and the like, and suitable salts of such groups include, for example, sulfonate, carboxylate, and phosphate salts. In other embodiments of formula VII, Y can be a radical that contains a basic group or a salt thereof, such as an ammonium, a phosphonium, or a sulfonium group. In some embodiments, the latent photoreactive group includes an aryl ketone or a quinone.

Exemplary crosslinking compounds of formula VII include 4,5-bis(4-benzoylphenylmethyleneoxy)benzene-1,3-disulfonic acid or salt; 2,5-bis(4-benzoylphenylmethyleneoxy)benzene-1,4-disulfonic acid or salt; 2,5-bis(4-benzoylmethyleneoxy)benzene-1-sulfonic acid or salt; N,N-bis[2-(4-benzoylbenzyloxy)ethyl]-2-aminoethanesulfonic acid or salt, and the like. See U.S. Pat. No. 6,278,018. The counter ion of the salt can be, for example, ammonium or an alkali metal such as sodium, potassium, or lithium. Other exemplary crosslinking compounds of formula VII include ethylenebis(4-benzoylbenzyldimethylammonium) salt; hexamethylenebis(4-benzoylbenzyldimethylammonium) salt; 1,4-bis(4-benzoylbenzyl)-1,4-dimethylpiperazinediium) salt, bis(4-benzoylbenzyl)hexamethylenetetraminediium salt, bis[2-(4-benzoylbenzyldimethylammonio)ethyl]-4-benzoylbenzylmethylammonium salt; 4,4-bis(4-benzoylbenzyl)morpholinium salt; ethylenebis[(2-(4-benzoylbenzyldimethylammonio)ethyl)-4-benzoylbenzylmethylammonium]salt; and 1,1,4,4-tetrakis(4-benzoylbenzyl)piperzinediium salt. See U.S. Pat. No. 5,714,360. The counter ion can typically be a carboxylate ion or a halide.

The coating composition can be applied to the surface of a medical device using any suitable technique. For example, the coating composition can be dipped, sprayed, sponged, or brushed on a device to form a layer, and then dried. In some modes of practice, the coating composition can be applied by dip-coating.

In other embodiments of the invention a compound of Formula I can be immobilized on a surface of an article and then a composition containing polymerizable material can be applied to the surface having the immobilized compound of Formula I, and then the surface can be treated to activate the UV photogroup, with the activated group serving as a polymerization initiator for the free-radical polymerization of the polymerizable material. Polymerization of the polymerizable material forms the polymeric matrix, such as a hydrophilic coating, on the surface of the article.

Hydrophilic polymerizable material can be hydrophilic monomers or polymerizable hydrophilic polymers ("macromers"). One or more free radically polymerizable groups, for example, unsaturated carbon-carbon bonds (—C═C—) such as vinyl groups can be present on the hydrophilic polymerizable material.

Polymerization of the hydrophilic polymerizable material can be by "grafting from" polymerization from a surface, "grafting through" polymerization, or both. In grafting from polymerization, a surface bound compound of Formula I can be activated to cause polymerization and formation of the coating. In grafting through polymerization, the compound of Formula I can be dispersed among the polymerizable material.

Various hydrophilic monomers such as acrylic monomers, vinyl monomers, ether monomers, or combinations of any one or more of these can be used to prepare the coating. Acrylic monomers include, for example, methacrylate, methyl methacrylate, hydroxyethyl methacrylate, hydroxyethyl acrylate, methacrylic acid, acrylic acid, glycerol acrylate, glycerol methacrylate, acrylamide, methacrylamide, and derivatives and/or mixtures of any of these. Vinyl monomers include, for example, vinyl acetate, vinylpyrrolidone, vinyl alcohol, and derivatives of any of these.

Hydrophilic crosslinking monomers having more than one unsaturated group can optionally be used in the coating composition. Hydrophilic crosslinking monomers include, for example, ethylene glycol dimethacrylate, diethylene glycol dimethacrylate, 2,3-propanediol dimethacrylate, 1,4-butanediol dimethacrylate, and allyl methacrylate.

Macromers include any pre-formed hydrophilic polymers, such as listed in Table 1, derivatized with one or more free-radically polymerizable group(s). Exemplary macromers can be based on one or more of the following polymers: poly(vinylpyrrolidone) (PVP), poly(ethylene oxide) (PEO), poly(ethyloxazoline), poly(propylene oxide) (PPO), poly(meth)acrylamide (PAA) and poly(meth)acylic acid, poly(ethylene glycol) (PEG) (see, for example, U.S. Pat. Nos. 5,410,016, 5,626,863, 5,252,714, 5,739,208 and 5,672,662) PEG-PPO (copolymers of polyethylene glycol and polypropylene oxide), hydrophilic segmented urethanes (see, for example, U.S. Pat. Nos. 5,100,992 and 6,784,273), and polyvinyl alcohol (see, for example, U.S. Pat. Nos. 6,676,971 and 6,710,126).

In some modes of practice, the total concentration of hydrophilic polymerizable material (hydrophilic monomers, macromers, or combinations thereof) is in the range of about 1% (w/v) to about 50% (w/v), or more specifically in the range about 1% (w/v) to about 5% (w/v), or about 5% (w/v) to about 40% (w/v).

The coating process can be carried out at a temperature suitable to provide a coating to the surface, or a portion of the surface, of a medical device. Generally, the coating process can be carried out at a temperature in the range of 10° C. to 50° C., and more specifically at a temperature in the range of 15° C. to 25° C. The actual coating temperature can be chosen based on aspects of the device surface to be coated, coating composition, including the coating composition solvent(s), the compound of Formula I, and the polymeric matrix-forming material, and also the method used to dispose the coating composition on the device surface.

A typical dip-coating procedure involves immersing the article to be coated in the coating composition, dwelling the object in the composition for a period of time (a standard time can be generally less than about 30 seconds, and can even be less that 10 seconds in many cases), and then removing the article from the composition. After the article has been dip-coated in the coating solution, it is optionally dried. Drying can be carried out using any suitable method, including air-drying the dip-coated article. Times up to 30 minutes can be sufficient to dry the coated article although shorter times may be also sufficient. In some cases, the article does not necessarily have to be dried before being irradiated after dip-coating (see Irradiation Process below)

In some embodiments of the present disclosure the coating process can be carried out to provide a coating having a desired thickness that can be suitable for the device being coated and the specific application for which the coated device is intended. Exemplary thicknesses of the coating in a dried state can be in the range of about 0.2 μm to about 5 μm. In some cases, the thickness of the coating can increase upon hydration of the polymeric material in the coating. For example, the coating can swell to a thickness in the range of about 1.1 to about 3 times the thickness of the coating in the dried state. Swelling can be minimized by increasing the amount of the compound of Formula I, and/or a second optional UV-activated crosslinker, in the coating composition.

Upon application of a composition to a device surface, a step of irradiating can be performed to activate the latent photoreactive groups to cause crosslinking of the hydrophilic polymers. Irradiation can be performed before and/or after the coated material dries on the surface of the device. Actinic radiation can be provided by any suitable light source that promotes activation of the photoreactive groups. Some light sources (such as those available from Dymax Corp.) provide UV irradiation in the range of about 190 nm to about 390 nm, and in some embodiments, from about 300 nm to about 350 nm. A suitable dose of radiation can be in the range of about 0.5 mW/cm$^2$ to about 2.0 mW/cm$^2$.

In another mode of practice, the polymeric matrix can be formed from a composition that includes a polymer made from a composition including the (monomer) compound of Formula I. Such a polymer made includes one or more groups having UV-activatable photogroups and fluorescence emitting stilbene groups that are pendent from the polymer's backbone. The UV-activatable photogroups pendent from the polymer's backbone can provide covalent bonding to other hydrophilic polymers in the coating, or to the device surface, in a manner like the crosslinking agent does as described herein.

The hydrophilic photo-polymer can have a hydrophilic backbone, such as according to any of those described in Table 1, with, for example, UV-activatable aryl ketones photogroups coupled to monomers of the backbone via a stilbene chemical moiety. Exemplary hydrophilic stilbene-containing photopolymers can be prepared by copolymerizing a compound of Formula I with one or more hydrophilic monomers. Exemplary monomers are selected from the group consisting methyl acrylate, methyl methacrylate, hydroxyethyl methacrylate, hydroxyethyl acrylate, hydroxypropyl acrylate, hydroxypropyl methacrylate, hydroxypropyl methacrylamide, acrylic acid, methacrylic acid, glyceryl acrylate, glyceryl methacrylate, methacrylamide, acrylamide, methacrylic acid, vinyl acetate, vinyl alcohol, methyl vinyl ether, (meth)-acrylamide derivatives, such as alkyl (meth)acrylamide and aminoalkyl(meth)acrylamide, such as aminopropylmethacrylamide and dimethylaminopropylmethacrylamide, and vinyl pyrrolidone.

The hydrophilic stilbene-containing photopolymer can be used alone or with one or more other different photopolymers, or one or more other non-photoderivitized polymer. For example, one particular composition uses a hydrophilic stilbene-containing photopolymer, a photo-PVP copolymer, and a (non-photoderivatized) PVP homopolymer or copolymer. The hydrophilic polymer can be used in a coating composition alone or with one or more other photopolymer, or non-photoderivitized polymers, at a total hydrophilic polymer concentration (one or more hydrophilic polymers) in the range of, for example, about 0.5% (w/v) to about 50% (w/v), or more specifically in the range about 1% (w/v) to about 30% (w/v), or about 2.5% (w/v) to about 20% (w/v).

After the coating has been formed on the surface of a device (such as a catheter, for example) the coated device can optionally be sterilized prior to use. While any type of sterilization procedure can be employed, one exemplary procedure involves treatment with ethylene oxide. The coated device can be obtained and subject to a sterilization process, such as ethylene oxide sterilization, or a user can perform the steps of forming a hydrophilic coating and then also perform sterilization of the coated device.

Optionally, a bioactive agent can be included in the polymeric matrix comprising the compound of Formula I. Bioactive agent can be held within or released from the coating to provide a therapeutic action in association with the device surface, such as to prevent infection, or treat a pre-existing condition at the location of insertion or implantation.

Exemplary bioactive agents include, but are not limited to, antibiotics, anti-microbials, anti-inflammatory agents, anti-proliferative agents, immunomodulatory agents, anti-mitotics, and anesthetics. Particularly useful bioactive agents of these classes include macrolide antibiotics such as rapamycin (triene macrolide antibiotic) and rapamycin analogs; immunomodulatory agents such as ABT-578; antimitotics including taxoid drugs such as paclitaxel and docetaxel; anti-inflammatory agents such as dexamethasone and betamethasone; and anesthetics such as lidocaine or tetracaine.

To exemplify the benefits that the coatings of the present invention provide to medical devices, a visualizable hydrophilic polymer coating on the surfaces of a cardiac catheter is discussed.

A cardiovascular catheter is typically a long cylindrically-shaped device made of a plastic material that for insertion into the vasculature of a patent, with the distal end of the catheter advanced through the vasculature to a target location. For example, a catheter is inserted into femoral artery in the groin or the radial artery in the wrist, and advanced into the chambers of the heart or into the coronary arteries. Typically, a guidewire is used to push the catheter to a target location in the body. Prior to insertion of the catheter, the coating, which fluoresces upon irradiation with UV light in the range of about 300 nm to 430 nm can be inspected. Exemplary light sources capable of providing irradiation in this wavelength include conventional fluorescent lamps, "black" lights, halogen lamps, fast halogen lamps, argon-ion lasers, plasma arc, LED (light emitting diode)-based sources. Light sources capable of providing light radiation in this wavelength are commercially available from, for example UVP (Upland, Calif.), Dymax (Torrington, Conn.), or EFOS, Inc. (Mississauga, Ontario, Canada).

The presence of the fluorescent compound of formula I in the coating enables visual assessment of coating quality, including thickness. The presence of the fluorescent compound can also be useful for determining if the coating includes any undesirable features or irregularities such as coating cracks or areas of delamination. Visualization of the polymeric material can be enhanced by reducing or eliminating the amount of background light.

A catheter with a visualizable hydrophilic polymer coating can be used for cardiac catheterization. Cardiac catheterization includes procedures such as coronary angiography, as well as left ventricle angiography. Once the catheter is in place, it can be used to perform any one of a number of procedures including angioplasty, angiography, and balloon septostomy. The visualizable hydrophilic polymer-coated catheter can be used in various analytic procedures, such as measuring blood pressure within the heart, blood oxygenation, and the contractile patterns and strength of cardiac muscle. The catheter can also be used in procedures to inject dye into the coronary arteries, such as coronary angiography or coronary arteriography. In this process, a catheter having the visualizable hydrophilic polymer coating can be inserted using a guidewire and advanced towards the heart to a position above the aortic valve. The guidewire can then be removed. The catheter can then be engaged with the origin of the coronary artery (either left main stem or right coronary artery) and x-ray opaque iodine-based contrast can be injected to make the coronary vessels show up on the x-ray fluoroscopy image. A visualizable hydrophilic polymer-coated catheter can also be used in balloon-based procedures such as coronary angioplasty (e.g., percutaneous coronary intervention; PCI).

As another example, a visualizable hydrophilic polymer coating can be formed on the surface of an endoscopic sheath. Endoscopic sheaths can be used in various medical procedures, including those involving the urogenital tract, the gastrointestinal tract, and the vasculature. For example an endoscope can be delivered through an endoscopic sheath. A visualizable hydrophilic polymer coating that is lubricious can facilitate movement of the sheath in the body as well as the device within the sheath.

Example 1

Preparation of 4-formylbenzophenone (compound 1)

Hexamine (16.91 g, 120.6 mmol) and chloroform ($CHCl_3$, 110 ml) were placed in a 250 mL round bottomed flask fitted with a magnetic stirrer and a soxhlet extractor. 4-bromomethylbenzophenone (BMBP; 30.0 g, 109 mmol) was placed in the extraction thimble. The reaction was refluxed for 4 hours (the BMBP was added within an hour). The reaction mixture was cooled and added to diethyl ether ($Et_2O$, 250 mL). The resultant sticky mass was broken up with a spatula and stirred for 30 minutes. The solid was collected on a sintered glass Buchner funnel, and washed with $Et_2O$ (2×100 mL). The solid was transferred to a 500 mL round bottomed flask along with water (109 mL) and acetic acid (109 mL). The solution was refluxed for 1 hour. Water (180 mL) and hydrochloric (Con HCl, 38 mL) were added and the reaction was refluxed for 5 minutes. The reaction mixture was cooled and extracted with $CHCl_3$ (3×100 mL). The solution was dried and evaporated to give an oil (4-formylbenzophenone, 15 g, 65% of theory), which solidified on standing. $^1H$ NMR (400 MHz, DMSO-$d_6$) $\delta$10.14 (s, 1H), 7.5-8.1 (m, 9H). The NMR analysis was consistent with the desired product.

Example 2

Preparation of diethyl (4-benzoylbenzyl) phosphonate (compound 2)

BMBP, 50.0 g, 181.8 mmol) and triethyl phosphite (150 mL, 875 mmol) were placed in a 500 mL round bottomed flask fitted with magnetic stirrer, gas outlet tube, thermowell, and a TEFLON sparge tube for nitrogen. The reaction was heated for 2 hours using an oil bath at 125° C. After about 6 minutes the reaction temperature reached a maximum temperature of 129° C. Applying a vacuum, volatiles were removed at 70° C. at 6 mm Hg pressure to give an oil (68.7 g). A sample of the residue (12 g) was placed in a short path distillation apparatus. The flask was heated at a pressure <1 mm Hg, and 1.25 g of distillate at 40° C. was collected. The distillation temperature dropped and the pot residue started to darken. The residual diethyl (4-benzoylbenzyl) phosphonate was cooled and used without further distillation in the 4,4'-dibenzoylstilbene preparation. $^1$H NMR (400 MHz, DMSO-$d_6$) δ 7.46-7.74 (m, 9H), 4.04-3.94 (m, 4H), 3.37 (d, J=22 Hz, 2H), 1.19 (s, J=7, 6H)

Example 3

Preparation of 4,4'-dibenzoylstilbene phosphonate (compound 3)

In a 50 mL round bottomed flask was placed dry DMSO (5.0 ml) along with NaH (235 mg of 60%, 5.88 mmol). When the $H_2$ gas evolution stopped, the stirred solution was placed in an ice bath. When DMSO started to freeze, diethyl (4-benzoylbenzyl) phosphonate (1.95 g, 5.87 mmol) and 4-formylbenzophenone (1.23 g, 5.85 mmol) in DMSO/THF-50/50 (30 mL) was added using a syringe pump set at 0.275 mL/minute (A few mls of the solution was inadvertently added before the ice bath was in place). During the addition a solid formed at the contact of each drop of the solution added. Additional swirling of the flask was done occasionally to keep the solid from building up at the point of entry. During the last few ml of addition the solid stopped forming. A second portion of NaH (24 mg) was added. The reaction was stirred magnetically during the reaction and for 30 minutes, after the additions were completed. The reaction mixture was poured into water (300 mL). A solid that formed was collected on a sintered glass funnel. The solid was resuspended and filtered 3 times in water (100 mL). The product was dried in a vacuum oven for >1 hour at 30° C. The product was left in the oven over the weekend (with KOH in the oven) at room temperature sealed under vacuum. The weight of isolated product was 2.19 g (96% of theory). Analysis by TLC $R_f$=0.27 [1% acetone in chloroform] gave a single spot, which was fluorescent under long wave UV. MS-ESI m/z 389 [M+H]$^+$ Example 4

Preparation of a Diaminostilbene-Disulfonic Acid Photo Derivative (Compound 5)

4-isocyanatobenzophenone (0.5 g) was added to a solution of benzenesulfonic acid, 2,2'-(1,2-ethenediyl)bis[5-[[4-[bis(2-hydroxyethyl)amino]-6-(phenylamino)-1,3,5-triazin-2-yl]amino]-, disodium salt (4193-55-9) (fluorescent brightener 28; Sigma) (1 g) in pyridine (40 mL). The reaction mixture was allowed to stir at ambient temperature and under nitrogen for 72 hr and then at 80° C. for 8 hr. At which point, pyridine was evaporated and the yellow solid was dried under vacuum. The crude product was purified on Yamazen AI-580S flash chromatography system using C18 column and acetonitrile/water eluent.

Example 5

Preparation of a Diaminostilbene-Disulfonic Acid Photo Derivative (Compound 6)

Benzoylbenzoic chloride (1.32 g) was dissolved in dry THF (10 mL). 4,4'-diaminostilbene-2,2'-disulfonic acid (1 g) was dissolved in 1M NaOH (14 mL) and water (5 mL) in a separate 50 mL round-bottom flask. Benzoylbenzoic chloride in THF was added over a period of 5 min to the solution of 4,4'-diaminostilbene-2,2'-disulfonic acid. Immediately, pale-yellow precipitate formed. The reaction was allowed to stir at ambient temperature for 2 hr. At which point, the precipitate was collected by vacuum filtration and washed with water.

Example 6

Coatings Incorporating a Diaminostilbene-Disulfonic Acid Photo Derivative (Compound 5)

A solution was prepared incorporating the fluorescent brightener 28-BBA reagent prepared in Example 4 above. The formulation used was 18/1/0.25 mg per mL photo-PVP/photo-crosslinker/compound 5 in 75%/25% IPA/water.

Short sections of samples were hand dip coated with 1 or 2 coats. Each coat was allowed to dry before UV curing for 30 seconds or 3 minutes. One of the samples was hydrated with water and finger rubbed up to 40 rubs. The samples were then observed under normal light and under long wave UV in a dark room. Pictures were taken in both instances to compare.

Figure 1A:
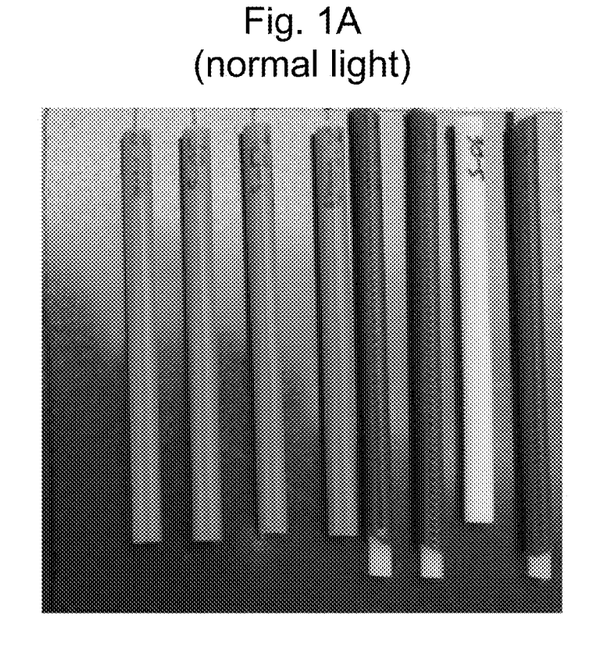
FIGS. 1A and 1B are pictures of PEBAX rods coated with polymeric compositions including fluorescent compounds of the invention.
Figure 1B:
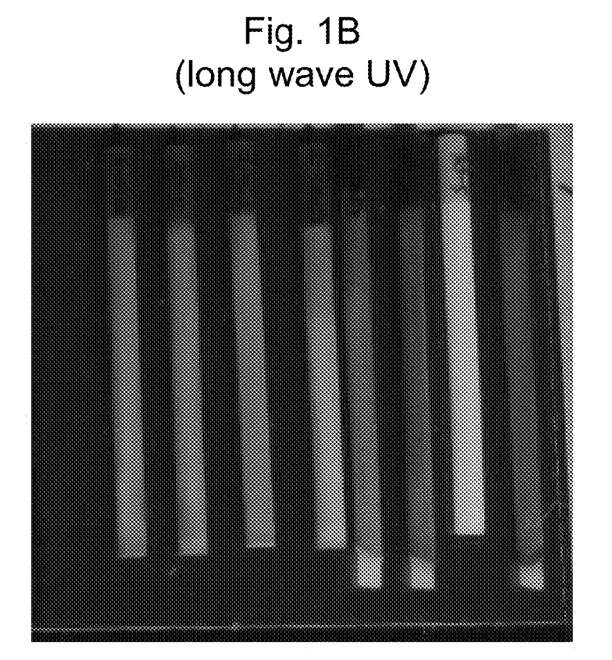

FIGS. 1A and 1B show coatings of the above formulations. Coated PEBAX samples include light blue 63D, dark blue (braided) 72D, and white 35D. The coated sections were visible under UV illumination on all samples including the rubbed sample.

Example 7

Preparation 4-benzoyl-4'-carboxystilbene (compound 7)

Sodium hydride (840 mg of 60% oil suspension, 21 mmol) was added to DMSO (5 mL). After the gas evolution stopped, THF (5 mL) was added, and the solution was cooled in an ice bath. A solution of 4-carboxybenzaldehyde (1.50 g, 10.0 mmol), Diethyl (4-benzoylbenzyl)phosphonate (3.32 g, 10 mmol), DMSO (25 mL), and THF (25 mL) was added to the stirred cold dimsyl sodium solution over 1 hour. After the addition was complete, the reaction was stirred for an additional 30 minutes. The reaction was poured into acetone (110 mL). The precipitate was isolated by filtration and resuspended in acetone (100 mL) followed by filtration two more times. The solid was dried in a vacuum oven at 40° C. to give 3.46 g of the sodium salt. The sodium salt was heated with 1N HCl (100 mL) for 30 minutes. The residue was isolated by filtration. The residue was resuspended in water (100 mL) followed by filtration 2 times. After drying, the crude product (2.9 g) was analyzed by HPLC-MS-ESI m/z 327.4 [M−H]−, 329.5 [M+H]+.

Example 8

Preparation (4-benzoyl-N-[3-(methacryloylamino)propyl]stilbene-4'-carboxamide) (compound 8)

Photo-carboxy-stilbene (1.00 g, 3.05 mmol), thionyl chloride (20 ml, 274 mmol), and DMF (50 mL, 0.65 mmol) were placed in a 50 ml RB flask. The reaction was refluxed with stirring for 1 hour. The volatiles were removed under vacuum to give the intermediate acid chloride. The acid chloride was transferred to a 100 ml RB flask with chloroform (40 mL). APMA-HCl (0.60 g, 3.36 mmol) was placed in a vial with chloroform (5.0 mL), saturated potassium carbonate (5.0 ml, ~30 mmol), and water (4.0 mL). The mixture was shaken for 1 minute, and then centrifuged to speed up separation. The chloroform layer was separated and passed through anhydrous sodium sulfate in a pipette filter. The aqueous layer was extracted with fresh chloroform (4.0 mL). The chloroform layer was again separated and dried with the same drying pipette filter. The chloroform solution of free based APMA was placed in an addition funnel and slowly (~20 minutes) added to the stirred acid chloride solution. The solution was hazy and allowed to stir overnight at room temperature. The reaction was placed in a separatory funnel along with water (50 mL) and con. HCl (0.83 ml, 10 mmol). The layers were separated, and the aqueous layer was extracted with chloroform (50 ml), chloroform/ethyl acetate (1:1, 50 mL), and 3 times with chloroform/isopropyl alcohol (9:1, 50 mL), The organic layers were combined and dried over sodium sulfate. A solution (10 µL) of phenothiazine (10 mg/mL in chloroform) was added to the dried chloroform solution before the volatiles were removed on a rotovap with an air bleed. The solid isolated (1.26 g) was analyzed by HPLC-MS indicating a majority of the desired product. MS-ESI m/z 453.8 $[M+H]^+$. A sample was purified on silica gel column using a hexane/ethyl acetate-9/91 to ethyl acetate gradient. The purified sample was ~96% pure by NMR analysis. $^1$H NMR (400 MHz, DMSO-$d_6$) δ 8.48 (t, J=5.6 Hz, 1H, amide proton), 7.94 (t, J=5.6 Hz, 1H, amide proton), 7.49-7.90 (m, 15H, aromatic and benzyl protons) 5.66 (s, 1H, vinyl proton), 5.32 (s, 1H, vinyl proton), 3.30 (m, 2H, methylene protons), 3.20 (m, 2H, methylene protons), 1.87 (s, 3H, methyl protons), 1.71 (m, 2H, central methylene protons).

What is claimed is:

1. A compound of Formula I:

wherein $R^{A1}$, $R^{A1'}$, $R^{A2}$, $R^{A2'}$ and are independently selected from the group consisting of H and —$SO_3R^1$; and wherein $R^1$ is independently selected from the group consisting of H, monovalent, and divalent metal cations; wherein $R^B$ and $R^{B'}$ are wherein $R^{14}$ and $R^{15}$ are independently selected from H, $R^{23}R^9$, and $R^{16}R^9$, and at least one of $R^{14}$ or $R^{15}$ is $R^{23}R^9$ or $R^{16}R^9$, with the proviso that both $R^{14}$ and $R^{15}$ are not H,
wherein $R^{23}$ is selected from the group consisting of a covalent bond, —C(O)—, —$CH_2$NHC(O)—, —$CH_2$OC(O)O—, —$CH_2$NHC(S)NH—, —$CH_2$OC(S)NH—, —$CH_2$NHC(O)O—, —$CH_2$NHC(O)NH—, —$CH_2$OC(O)—, and —C(O)O—;
wherein $R^{16}$ is selected from the group consisting of a covalent bond, —C(O)—, —NHC(O)—, —OC(O)O—, —NHC(S)NH—, —OC(S)NH—, —NHC(O)O— and —NHC(O)NH—, —C(O)O—, —OC(O)—, and —C(O)NH; and
wherein $R^9$ is selected from a photochemically reactive diaryl ketone group optionally ring substituted, a thermochemically reactive group selected from the group consisting of aryl azides, acyl azides, azido formats, phosphoryl azides, diazoalkanes, diazoketones, diazirines, ketenes, dialkyl peroxides, diacyl peroxides, and peroxyesters, or a free radical polymerizable group selected from acrylate, methacrylate, hydroxyethyl methacrylate, hydroxyethyl acrylate, hydroxypropyl acrylate, hydroxypropyl methacrylate, glyceryl acrylate, glyceryl methacrylate, acrylamino, methacrylamino, alkyl(meth)acryl amino, aminoalkyl(meth)acryl amino, vinyl ether, and vinyl ester.

2. The compound of claim 1 where $R^9$ is a diaryl ketone group, optionally ring substituted.

3. The compound of claim 1 where $R^{14}$ and $R^{15}$ are independently selected from H and $R^{16}R^9$.

4. The compound of claim 3 wherein $R^9$ is a diaryl ketone group having the structure:

5. The compound of claim 3 wherein $R^{16}$ is —C(O)—.
6. The compound of claim 3 having the structure: